United States Patent
White et al.

(10) Patent No.: US 9,809,518 B2
(45) Date of Patent: Nov. 7, 2017

(54) FEED SOURCES FOR BUTANEDIOL PRODUCTION PROCESSES

(71) Applicant: Lyondell Chemical Technology, L.P., Houston, TX (US)

(72) Inventors: Daniel F. White, Houston, TX (US); Roberto Alvarez, Houston, TX (US); Beaven S. Mandimutsira, Sugar Land, TX (US)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

(21) Appl. No.: 15/352,851

(22) Filed: Nov. 16, 2016

(65) Prior Publication Data

US 2017/0144951 A1   May 25, 2017

Related U.S. Application Data

(60) Provisional application No. 62/258,189, filed on Nov. 20, 2015.

(51) Int. Cl.
*C07C 45/50* (2006.01)
*C07C 29/00* (2006.01)
*C07C 29/141* (2006.01)

(52) U.S. Cl.
CPC .......... *C07C 29/141* (2013.01); *C07C 45/50* (2013.01)

(58) Field of Classification Search
CPC .............................. C07C 45/50; C07C 29/141

USPC ................................................. 568/862, 908
See application file for complete search history.

(56) References Cited

U.S. PATENT DOCUMENTS

| 4,083,882 A | 4/1978 | Taylor et al. |
| 5,262,371 A * | 11/1993 | Faraj .................... B01J 27/1806 502/208 |
| 5,426,250 A | 6/1995 | Chen et al. |
| 7,847,135 B1 | 12/2010 | White |
| 2014/0005440 A1 | 1/2014 | Mandimutsira et al. |

FOREIGN PATENT DOCUMENTS

| WO | WO-2011053671 A1 | 5/2011 |
| WO | WO-2013181255 A1 | 12/2013 |

OTHER PUBLICATIONS

The International Search Report and Written Opinion for PCT/US2016/062229 dated Feb. 8, 2017.

* cited by examiner

*Primary Examiner* — Sikarl Witherspoon

(57) ABSTRACT

Butanediol production processes are described herein. In some embodiments, the processes include contacting an allyl alcohol stream with a hydroformylation catalyst in the presence of a gas stream including carbon monoxide and hydrogen under hydroformylation conditions sufficient to form a hydroformylation product stream including a butanediol intermediate, wherein the allyl alcohol stream includes less than 98 wt. % allyl alcohol.

11 Claims, 1 Drawing Sheet

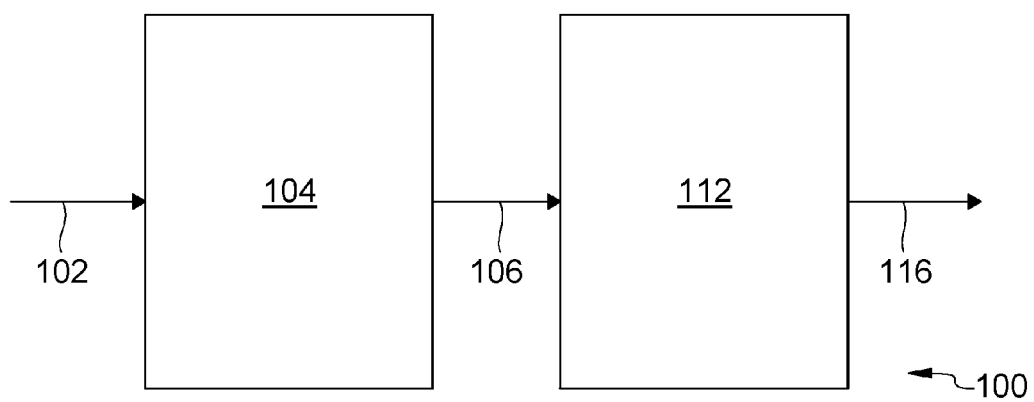

FEED SOURCES FOR BUTANEDIOL PRODUCTION PROCESSES

CROSS-REFERENCE TO RELATED APPLICATIONS

This application claims the benefit of priority to U.S. Provisional Application No. 62/258,189, filed on Nov. 20, 2015, which is incorporated herein by reference in its entirety.

FIELD OF THE INVENTION

The present disclosure relates to the production of butanediol. In particular, embodiments contained herein relate to feed sources for butanediol production processes.

BACKGROUND OF THE INVENTION

Butanediol production processes often include a two-step process. For example, such processes may include contacting an allyl alcohol stream with a hydroformylation catalyst in the presence of a gas stream to form an intermediate and hydrogenating the intermediate in the presence of a hydrogenation catalyst to form butanediol. Crude (i.e., unpurified) allyl alcohol streams may contain an appreciable level of impurities. Such impurities may be separated from the allyl alcohol prior to use in subsequent processes, such as butanediol production processes. However, the impurities can be difficult to separate from the allyl alcohol itself.

SUMMARY OF THE INVENTION

The present disclosure relates to butanediol production processes. In some embodiments, the processes include contacting an allyl alcohol stream with a hydroformylation catalyst in the presence of a gas stream including carbon monoxide and hydrogen under hydroformylation conditions sufficient to form a hydroformylation product stream including a butanediol intermediate, wherein the allyl alcohol stream includes less than 98 wt. % allyl alcohol. In some embodiments, the present technology relates to a multi-step process wherein an allyl alcohol feedstream is contacted with a transition metal catalyst complex such as a rhodium phosphate catalyst complex capable of hydroformylating the allyl alcohol feedstream, followed by further introduction of a crude (unpurified) allyl alcohol fraction for increasing the product stream(s). In further embodiments, the product stream(s) comprise aldehydes, esters and/or acrylates including but not limited to hydroxybutanal (HBA) and methylhydroxypropanal (MHPA).

One or more embodiments include the process of the preceding paragraph, further including contacting the butanediol intermediate with a hydrogenation catalyst in the presence of hydrogen under hydrogenation conditions sufficient to form a hydrogenation product stream including 1,4 butanediol.

One or more embodiments include the process of any preceding paragraph exhibiting an allyl alcohol conversion in a range of 80% to 100%.

One or more embodiments include the process of any preceding paragraph exhibiting selectivity in a range of 65% to 100%.

One or more embodiments include the process of any preceding paragraph, further including recovering 1-4 butanediol from the hydrogenation product stream.

One or more embodiments include the process of any preceding paragraph, wherein the allyl alcohol stream includes one or more impurities selected from acetone, water, propionaldehyde, n-propanol, $C_{4+}$ hydrocarbons, $C_{1+}$ oxygenates and combinations thereof.

One or more embodiments include the process of any preceding paragraph, wherein the allyl alcohol stream includes an acetone concentration in a range of 0 wt. % to 25 wt. % based on the total weight of the allyl alcohol stream, a water concentration in a range of 0 wt. % to 6 wt. % based on the total weight of the allyl alcohol stream, a propionaldehyde concentration in a range of 0 wt. % to 6 wt. % based on the total weight of the allyl alcohol stream, a n-propanol concentration in a range of 0 wt. % to 1 wt. % based on the total weight of the allyl alcohol stream, a $C_{4+}$ hydrocarbon concentration in a range of 0 wt. % to 5 wt. % based on the total weight of the allyl alcohol stream and oxygenates concentration in a range of 0 wt. % to 11 wt. % based on the total weight of the allyl alcohol stream.

One or more embodiments include the process of any preceding paragraph, wherein the allyl alcohol stream includes methanol in a methanol concentration of less than 100 ppm.

One or more embodiments include the process of any preceding paragraph, wherein the allyl alcohol stream includes an acetone concentration of at least 0.25 wt. % based on the total weight of the allyl alcohol stream, a methanol concentration of less than 100 ppm based on the total weight of the allyl alcohol stream, a water concentration of at least 0.1 wt. % based on the total weight of the allyl alcohol stream, a propionaldehyde concentration of at least 0.25 wt. % based on the total weight of the allyl alcohol stream, or combinations thereof.

One or more embodiments include the process of any preceding paragraph, wherein the hydroformylation conditions include a hydroformylation temperature in a range of 20° C. to 100° C. and a hydroformylation pressure in a range of 20 psig (137,895 Pa) to 600 psig (4,136,854 Pa).

One or more embodiments include the process of any preceding paragraph, wherein the hydroformylation catalyst includes rhodium phosphate.

While multiple embodiments are disclosed, still other embodiments will become apparent to those skilled in the art from the following detailed description. As will be apparent, certain embodiments, as disclosed herein, are capable of modifications in various aspects without departing from the spirit and scope of the claims as presented herein. Accordingly, the drawings and detailed description are to be regarded as illustrative in nature and not restrictive.

BRIEF DESCRIPTION OF THE DRAWINGS

The claimed subject matter may be understood by reference to the following description taken in conjunction with the accompanying drawings, in which like reference numerals identify like elements, and in which:

The FIGURE illustrates a schematic of one or more embodiments of the disclosed processes.

While the claimed subject matter is susceptible to various modifications and alternative forms, the drawings illustrate specific embodiments herein described in detail by way of example. It should be understood, however, that the description herein of specific embodiments is not intended to limit the claimed subject matter to the particular forms disclosed, but on the contrary, the intention is to cover modifications, equivalents, and alternatives falling within the spirit and scope as defined by the appended claims.

DETAILED DESCRIPTION OF THE INVENTION

Illustrative embodiments of the subject matter claimed below will now be disclosed. In the interest of clarity, not all features of an actual implementation are described in this specification. It will be appreciated that in the development of any such actual embodiment, numerous implementation-specific decisions can be made to achieve the developers' specific goals, such as compliance with system-related and business-related constraints, which will vary from one implementation to another. Moreover, it will be appreciated that such a development effort, even if complex and time-consuming, would be a routine undertaking for those of ordinary skill in the art having the benefit of this disclosure.

The embodiments illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. Further, various ranges and/or numerical limitations may be expressly stated below. It should be recognized that unless stated otherwise, it is intended that endpoints are to be interchangeable with one another to form additional ranges that may or may not be expressly stated herein. Further, any ranges include iterative ranges of like magnitude falling within the expressly stated ranges and are further understood to set forth every number and range encompassed within the broader range of values. When such ranges are absent an upper endpoint (or in the alternative, a lower endpoint), it is contemplated that such endpoint is the feasible maximum value (or in the alternative, the feasible minimum value). Further, in the description below, unless otherwise specified, the compounds described herein may be substituted or unsubstituted and the listing of compounds includes derivatives thereof.

Propylene oxide (PO) is a valuable chemical that can be used to produce a variety of other chemicals, including, but not limited to, propylene glycol, propylene glycol ethers, 1,4 butanediol (BDO), and polyols, for example. Processes for producing propylene oxide are known in the art and, as such, are not discussed in detail herein. However, one process of forming propylene oxide includes reacting propylene with an oxidizing agent in the presence of a catalyst. Non-limiting examples of the oxidizing agent include organic hydroperoxides (e.g., ethyl benzene hydroperoxide, cumene hydroperoxide and tert-butyl hydroperoxide) and hydrogen peroxide, for example. Non-limiting examples of the catalyst include solubilized molybdenum catalysts, heterogeneous titania-on-silica catalysts, and titanium silicate catalysts, for example.

Propylene oxide streams may be utilized in isomerization processes to form allyl alcohol. For example, one or more embodiments include isomerization of one or more propylene oxide streams in the presence of an isomerization catalyst under isomerization conditions to form an isomerization product including allyl alcohol. Isomerization processes are known in the art and can include slurry and/or gas phase processes. However, one or more embodiments include slurry phase isomerization. In slurry phase isomerization, the isomerization catalyst is suspended in an inert liquid (i.e., to form a catalyst slurry) and the propylene oxide is introduced to the catalyst slurry to react and form allyl alcohol. The inert liquid may include any hydrocarbon or mixture thereof which will remain liquid, and is non-reactive and thermally stable, at the isomerization conditions employed. Illustrative, non-limiting examples of the inert liquid include high boiling temperature oils (i.e., those having a boiling temperature greater than the isomerization temperature) including, but not limited to $C_{12}$ or greater alkylaromatic hydrocarbons, such as dodecyl benzene or mixtures of alkylaromatic hydrocarbons, such as $C_{14}$-$C_{30}$ alkylaromatic hydrocarbons (e.g., Therminol® 55, a product of Solutia, Inc.), for example.

Isomerization catalysts are known in the art and illustrative, non-limiting examples can include lithium phosphate catalysts. For example, the lithium phosphate catalysts may include lithium phosphate supported on an inert supporting material. An inert supporting material is one, which itself, does not catalyze under isomerization conditions. Such inert support materials may include talc, inorganic oxides, clays and clay minerals, ion-exchanged layered compounds, diatomaceous earth compounds, zeolites, resinous support materials, such as a polyolefin, or combinations thereof, for example. Specific inorganic oxides include silica, alumina, magnesia, titania, zirconia and combinations thereof (e.g., silica-alumina and aluminosilicates).

The isomerization catalyst may include lithium phosphate and optional inert support in any amount desired for the isomerization reaction. However, in one or more embodiments, wherein the isomerization catalyst includes the inert support, the isomerization catalyst may include a lithium phosphate concentration in a range of 5 wt. % to 60 wt. %, or 10 wt. % to 55 wt. %, or 15 wt. % to 75 wt. % and a support concentration in a range of 40 wt. % to 95 wt. %, or 45 wt. % to 90 wt. %, or 25 wt. % to 85 wt. %, based on the total weight of isomerization catalyst.

In addition, the lithium phosphate catalyst may include additional components, such as sodium, boron or combinations thereof, for example. For example, the lithium phosphate catalyst may include boron in a boron concentration in a range of 0.03 wt. % to 1 wt. %, or 0.1 wt. % to 0.8 wt. % based on the total weight of the lithium phosphate catalyst. The lithium phosphate catalyst may include sodium in a sodium concentration in a range of 0.01 wt. % to 1 wt. %, or 0.02 wt. % to 0.8 wt. % based on the total weight of the lithium phosphate catalyst, for example. The lithium phosphate catalyst may have a boron:lithium molar ratio in a range of 0.001:1 to 0.05:1, or 0.003:1 to 0.03:1, or 0.007:1 to 0.02:1, for example. The lithium phosphate catalyst may have a sodium:lithium molar ratio in a range of 0.0002:1 to 0.02:1, or 0.003:1 to 0.01:1, for example. See, U.S. Pat. No. 6,803,491, which is incorporated in its entirety herein.

In one or more embodiments, the isomerization catalyst may contact the propylene oxide stream in an amount in a range of 1 wt. % to 30 wt. %, or 4 wt. % to 20 wt. %, or 6 wt. % to 15 wt. % based on the total weight of the isomerization reaction mixture (e.g., the "isomerization reaction mixture" includes the components of the propylene oxide stream and the isomerization catalyst, as well as any other minor components known in the relevant art), for example.

In practice, isomerization reaction conditions vary depending upon reaction parameters, reactor size and charge and the individual components employed. However, in one or more embodiments, the isomerization conditions may include an isomerization temperature in a range of 200° C. to 300° C., or 240° C. to 280° C., or 230° C. to 270° C., for example and an isomerization pressure in a range of 0 psig (0 Pa) to 30 psig (206,842 Pa), or 0 psig (0 Pa) to 15 psig (103,421 Pa) or 5 psig (34,474 Pa) to 10 psig (68,948 Pa), for example.

Isomerization processes may further include recovering the formed allyl alcohol from the isomerization product for use in subsequent processes. Many commercial processes utilize allyl alcohol for the manufacture of 1,4 butanediol (BDO) (referred to herein interchangeably with "butanediol production processes"). Allyl alcohol may also be used as a hydroxyl functional monomer in the polymer industry. For instance, allyl alcohol can be used for producing styrene-allyl alcohol copolymers and hydroxyl acrylic resins, for example.

As with other processes, the isomerization product may include a variety of impurities (e.g., as a result of side-chain reactions). Impurities are defined herein as any component in a process stream other than the targeted product itself (e.g., allyl alcohol is the targeted product in the isomerization product stream). For example, the impurities present in the isomerization product may include n-propanol, $C_{4+}$ hydrocarbons, $C_{1+}$ oxygenates, acrolein or combinations thereof, as well as other compounds other than the allyl alcohol, depending on the specific process. Furthermore, the isomerization product may include one or more impurities present in the isomerization feed depending on the level of purity of the propylene oxide stream (e.g., as a result of unreacted feedstock). For example, the isomerization product may include propionaldehyde, water, acetone, acetaldehyde, methyl formate or combinations thereof, for example.

Such impurities may been separated from the allyl alcohol prior to use in subsequent processes. Such separation processes are known in the art and can include separating one or more of the impurities from the allyl alcohol within a process stream (wherein the process stream may be referred to as "impure allyl alcohol") to form purified allyl alcohol via one or more methods, including, but not limited to, extraction, distillation, extractive distillation, caustic treatment, scavenging, adsorption and combinations thereof, for example. As used herein, the term "purified allyl alcohol" refers to an allyl alcohol stream having an allyl alcohol concentration of at least 98 wt. % based on the total weight of the allyl alcohol stream. It is to be noted that use of the term "allyl alcohol stream" herein refers to any stream containing allyl alcohol. The specific components and concentrations present in the respective allyl alcohol stream will be clear based on the discussion thereof.

While many processes exist for the separation of the impurities, such processes can be difficult to implement and/or are costly. Thus, continuous efforts have been underway to improve and develop methods to separate these impurities from allyl alcohol. However, embodiments described herein provide for use of impure allyl alcohol streams in subsequent processes, and in particular, in butanediol production processes, without the need for purification (or "substantial purification") of the allyl alcohol stream prior to use in butanediol production processes, and in particular in hydroformylation. As utilized herein, "impure allyl alcohol streams" are defined as allyl alcohol streams having an allyl alcohol concentration of less than 98 wt. % based on the total weight of the impure allyl alcohol stream. For example, the impure allyl alcohol streams may include an allyl alcohol concentration in a range of 90 wt. % to 98 wt. %, or 92 wt. % to 97 wt. % based on the total weight of the allyl alcohol stream. The impure allyl alcohol stream(s) may include crude allyl alcohol streams as well as other allyl alcohol streams including the specified total impurity concentration. Further, the term "substantial purification" provides for the inclusion of separation of one or more components from an allyl alcohol feed but at a level that is less than that required to provide for purified allyl alcohol.

While it is noted that the term "impurities" include one or more individual, discrete impurity components, each specified concentration range for each separate impurity component may include a concentration in a range of 0 wt. % to an upper limit. While in view of each discrete impurity component concentration recited it may appear that the total impurity concentration may be 0 wt. %, it would be appreciated by one skilled in the art that with the specified total impurity concentration, each discrete impurity component could not be present in the specified process stream, such as the impure allyl alcohol stream, at a level lower than that such that the specified process stream has a total impurity concentration less than that specified. However, each discrete impurity component may or may not be present in the specified process stream.

Thus, in one more embodiments, the impure allyl alcohol stream may include acetone at an acetone concentration in a range of 0 wt. % to 25 wt. %, or 0 wt. % to 5 wt. %, or at least 0.25 wt. %, or 0.8 wt. % to 2 wt. % based on the total weight of the impure allyl alcohol stream, for example. The impure allyl alcohol stream may include water at a water concentration in a range of 0 wt. % to 6 wt. %, or 0 wt. % to 1 wt. %, or at least 0.1 wt. %, or 0.1 wt. % to 0.5 wt. % based on the total weight of the impure allyl alcohol stream, for example. The impure allyl alcohol stream may include propionaldehyde at a propionaldehyde concentration in a range of 0 wt. % to 6 wt. %, or 0 wt. % to 5 wt. %, or at least 0.25 wt. %, or 0.8 wt. % to 2 wt. % based on the total weight of the impure allyl alcohol stream, for example. The impure allyl alcohol stream may include n-propanol at a propanol concentration in a range of 0 wt. % to 1 wt. %, or 0.25 wt. % to 0.5 wt. %, or at least 0.2 wt. % based on the total weight of the impure allyl alcohol stream, for example. The impure allyl alcohol stream may include $C_{4+}$ hydrocarbons at a $C_{4+}$ concentration in a range of 0 wt. % to 5 wt. %, or 100 ppm to 1 wt. %, or at least 100 ppm based on the total weight of the impure allyl alcohol stream, for example. The impure allyl alcohol stream may include $C_{1+}$ oxygenates at a $C_{1+}$ concentration in a range of 0 wt. % to 11 wt. %, or 0 wt. % to 5 wt. %, or 0.1 wt. % to 2 wt. %, or at least 0.1 wt. % based on the total weight of the impure allyl alcohol stream, for example.

As discussed briefly above, embodiments described herein provide for use of impure allyl alcohol streams in butanediol production processes without the need for substantial purification thereof. Thus, it is contemplated that the impure allyl alcohol may not undergo purification/recovery at a level such that the majority of all impurities are separated from the allyl alcohol. However, at least some portion of the components present in the impure allyl alcohol stream may be removed therefrom prior to use in subsequent processes. For example, one or more components selected from unreacted propylene oxide, catalyst residuals and/or one or more impurities, such as methanol, may be separated from the impure allyl alcohol stream prior to subsequent use thereof. Such separation processes are known in the art and can include separating one or more of the components from the allyl alcohol within a first impure allyl alcohol stream to form a second impure allyl alcohol stream via one or more methods, including, but not limited to extraction, distillation, extractive distillation, caustic treatment, scavenging, adsorption and combinations thereof, for example.

In one or more embodiments, the second impure allyl alcohol stream includes a propylene oxide concentration of less than 5 wt. %, or less than 3 wt. %, or less than 1 wt. % based on the total weight of the second impure allyl alcohol stream and a methanol concentration of less than 100 ppm, or less than 50 ppm, or less than 25 ppm based on the total weight of the second impure allyl alcohol stream. It will be within the capabilities of the skilled artisan to adjust separation conditions as needed to accomplish the above separations.

Butanediol production processes may include a hydroformylation reaction followed by hydrogenation. In the hydroformylation reaction, allyl alcohol (in the embodiments described herein, fed to the reaction via an impure allyl alcohol stream) may be contacted with a hydroformylation catalyst in the presence of a gas stream, such as a $CO/H_2$ gas mixture, under hydroformylation conditions sufficient to form a hydroformylation product including a BDO intermediate. The BDO intermediate may include a variety of components. Such components will vary depending upon the specific hydroformylation conditions and components of the allyl alcohol stream. However, in one or more embodiments, the BDO intermediate includes 4-hydroxybutyraldehyde.

The hydroformylation reaction may occur in the presence of a solvent. Solvents may include, but are not limited to those that are capable of solubilizing the hydroformylation catalyst but not reactive to other components produced in the hydroformylation reaction. Illustrative, non-limiting examples of solvents include compounds having low or minimal solubility in water, such as $C_4$-$C_{20}$ aliphatic hydrocarbons, $C_6$-$C_{20}$ aromatic hydrocarbons, $C_6$-$C_{20}$ halogenated aromatic hydrocarbons and ethers, such as toluene, cyclohexane and methyl t-butyl ether, for example.

Hydroformylation catalysts are known in the art and illustrative, non-limiting examples include rhodium based catalysts, for example. The hydroformylation catalyst may include rhodium in a rhodium concentration in a range of 10 ppm to 1000 ppm, or 50 ppm to 500 ppm, or 100 ppm to 200 ppm based on the total weight of the hydroformylation catalyst, for example. In one or more embodiments, the hydroformylation catalyst may include additional components, such as phosphine, for example. The hydroformylation catalyst may have a phosphine:rhodium molar ratio greater than 1:1, or greater than 1.2:1, or greater than 1.5:1, for example.

Rhodium based catalysts are known in the art and illustrative, non-limiting examples include $RhH(CO)_n(PR_3)_3$, $RhX(CO)_n(PR_3)_2$; $RhX(PR_3)_3$, wherein n is 1 or 2, X represents a halogen atom, $PR_3$ represents an organic tri-substituted phosphine and R represents an alkyl, aryl, alkoxy or aryloxy group, each R the same or different. Illustrative, non-limiting examples of tri-substituted phosphines include tributylphosphine, tricyclohexylphosphine, trioctylphosphine, triphenolphosphine, tritolylpospine, methyldiphenylphosphine, ethyl-n-pentylphenylphosphine, tributoxyphosphine and triphenoxyphosphine, for example.

In practice, hydroformylation reaction conditions vary depending upon reaction parameters, reactor size and charge and the individual components employed. However, in one or more embodiments, the hydroformylation conditions are fairly mild in an effort to favor the formation of linear rather than branched reaction products. For example, the hydroformylation conditions may include a hydroformylation temperature in a range of 20° C. to 100° C., or 60° C. to 80° C., or 60° C. to 70° C. and a hydroformylation pressure in a range of 20 psig (137,895 Pa) to 600 psig (4,136,854 Pa), or 30 psig (206,843 Pa) to 300 psig (2,068,427 Pa), or 35 psig (241,317 Pa) to 135 psig (930,792 Pa), for example.

The molar ratio of $CO:H_2$ contacting the hydroformylation catalyst may vary considerably, but in one or more embodiments may be about 1:1, or may be in a range of 1:3 to 3:1, or 1:9 to 9:1, for example. The reaction time for the hydroformylation reaction is such that the predominance of the allyl alcohol reacts.

Upon reaction and formation of the hydroformylation product, the hydroformylation catalyst may be separated from the BDO intermediate via known methods, such as extraction, to form a hydrogenation feed including the BDO intermediate, which may then be hydrogenated over a hydrogenation catalyst in the presence of hydrogen (and optional solvent) under hydrogenation conditions to form a hydrogenation product including the BDO.

Hydrogenation catalysts are known in the art and illustrative, non-limiting examples include Group VII and Group X metal catalysts. For example, hydrogenation catalysts may include nickel, cobalt, ruthenium, platinum, palladium, copper, zinc, chromium, alloys thereof or combinations thereof.

In one or more embodiments, the hydrogenation catalyst may contact the hydrogenation feed in an amount in a range of 0.1 wt. % to 15 wt. %, or 0.2 wt. % to 10 wt. %, or 0.3 wt. % to 3.3 wt. % based on the total weight of hydrogenation reaction mixture (e.g., the "hydrogenation reaction mixture" includes the components of the hydrogenation feed and the hydrogenation catalyst, as well as any other minor components known to ones skilled in the art), for example.

As briefly mentioned above, the hydrogenation may occur in the presence of solvent. Such solvent may be the same or different from those solvents previously described herein with reference to hydroformylation. When the same, such solvent may be added to the hydrogenation reaction or may be present in the hydrogenation feed as a result of the hydroformylation reaction.

In practice, hydrogenation reaction conditions vary depending upon reaction parameters, reactor size and charge and the individual components employed. However, in one or more embodiments, the hydrogenation conditions are more severe than those utilized for hydroformylation. For example, the hydrogenation temperature may be in a range of 60° C. to 200° C., or 80° C. to 140° C., or 90° C. to 110° C. and the hydrogenation pressure may be in a range of 200 psig to 1500 psig, or 300 psig to 1250 psig, or 500 psig to 1000 psig, for example. The reaction time for the hydrogenation reaction is such that the predominance of the BDO intermediate reacts.

Embodiments of the present technology provide for allyl alcohol production processes that exhibit allyl alcohol conversion rates that are similar to those utilizing purified allyl alcohol. For example, the butanediol production processes may exhibit an allyl alcohol conversion rate in a range of at least 80%, or at least 85%, or at least 90%, or at least 95%, or 80% to 100%. The allyl alcohol conversion can be used to evaluate the activity or efficiency of the respective catalysts and may be calculated via the following equation: conversion (%)=allyl alcohol reaction (wt.)/allyl alcohol fed (wt.)*100. Embodiments of the present technology further provide for butanediol production processes exhibiting a selectivity that is similar to those utilizing purified allyl alcohol. For example, the butanediol production processes may exhibit a selectivity in a range of at least 65%, or at least 70%, or at least 75%, or at least 80%, or at least 85%, or at least 90%, or at least 95%, or 65% to 100%. The term "selectivity" refers to the percentage of input/reactant converted to a desired output/product (i.e., allyl alcohol converted to 1,4 butanediol in the butanediol production processes).

Butanediol production processes may further include recovering the formed BDO from the hydrogenation product. Such recovery can be accomplished by methods which may include, without limitation, separation and/or purification processes (including, but not limited to, flashing, extraction and distillation). Such processes are known in the relevant art and therefore are not described in detail herein.

The FIGURE illustrates a schematic of an embodiment of a specific, non-limiting embodiment of a butanediol production process 100. The butanediol production process may include feeding an impure allyl alcohol stream 102 to a hydroformylation reactor 104 having a hydroformylation catalyst disposed therein to form a hydroformylation product stream 106. The allyl alcohol present in the impure allyl alcohol stream 102 contacts the hydroformylation catalyst within the hydroformylation reactor 104 at hydroformylation conditions sufficient to form a BDO intermediate, which is withdrawn from the hydroformylation reactor 104 via the hydroformylation product stream 106.

The butanediol production process 100 further includes introducing the hydroformylation product stream 106 to a hydrogenation zone 112 having a hydrogenation catalyst disposed therein to for a hydrogenation product stream 116. The BDO intermediate present in the hydroformylation product stream 106 contacts the hydrogenation catalyst within the hydrogenation zone 112 at hydrogenation conditions sufficient to form butanediol, which is withdrawn from the hydrogenation zone 112 via the hydrogenation product stream 116.

EXAMPLES

To facilitate a better understanding of the disclosure, the following examples of embodiments are given. In no way should the following examples be read to limit, or to define, the scope of the appended claims.

Various allyl alcohol streams were hydroformylated to determine the resultant products therefrom. The hydroformylation was carried out by adding a rhodium complex (1 equivalent, $4.3 \times 10^{-5}$ moles) to a solution a dry degassed toluene (15 g) and 2 equivalents trans-1,2-bis[di(3.5-dimethylphenyl)phosphinomethyl]cyclobutane. The resulting solution was then transferred to a 50 mL Parr autoclave. The autoclave was then flushed three times with a 1:1 $CO/H_2$ mixture and pressurized to 180 psig (1,241,056 Pa) and the autoclave was heated with stirring to the indicated temperature (e.g., 65° C.). Once the indicated temperature was attained for at least 5 minutes, crude allyl alcohol (3.5 mL) was injected and the autoclave pressure increased to 200 psig with the $CO:H_2$ mixture. The reactor was then maintained at a constant 200 psig (1,378,951 Pa) pressure and the gas uptake with time was monitored until there was no further gas uptake. The reactor was cooled down, depressurized and the solution was analyzed by gas chromatography to determine the products of the reaction. The same experiment was repeated with refined, commercially available allyl alcohol as feed. The results are illustrated in Table 1 below.

TABLE 1

| | Feed Stream | | Product Stream | |
|---|---|---|---|---|
| Component | Crude Allyl Alcohol | Purified Allyl Alcohol | Crude Allyl Alcohol | Purified Allyl Alcohol |
| Propylene Oxide | 0.08 | 0.00 | 0.01 | 0.00 |
| Propionaldehyde | 1.24 | 0.00 | 0.35 | 0.00 |
| Acetone | 1.29 | 0.00 | 0.17 | 0.00 |
| Acrolein | 0.10 | 0.01 | 0.00 | 0.00 |
| Methacrolein | 0.19 | 0.00 | 0.02 | 0.03 |
| Isopropanol | 0.01 | 0.00 | 0.05 | 0.01 |
| N-Propanol | 0.28 | 0.28 | 0.09 | 0.11 |
| Allyl Alcohol | 96.17 | 99.71 | 0.03 | 0.06 |
| 1-allyloxy-propan-2-01 | 0.85 | 0.00 | | |
| HBA | 0.00 | 0.00 | 19.24 | 23.40 |
| MHPA | 0.00 | 0.00 | 2.15 | 2.18 |
| BDO | 0.00 | 0.00 | 0.00 | 0.00 |
| Gamma Butyrolactone | | | 0.39 | 0.10 |
| Tetrahydrofuran | | | 0.11 | 0.14 |

*Note:
all values are weight percent based on the total weight of the stream, with the exception as those identified as ppm
HBA = hydroxybutanal,
MHPA = methylhydroxypropanal,
BDO = butanediol It was observed that sufficient conversion rates were obtained with the "impure allyl alcohol" stream, while the resulting product streams further included levels of impurities that are not anticipated to significantly affect subsequent processes.

What is claimed is:

1. A process comprising:
contacting an allyl alcohol stream with a hydroformylation catalyst comprising rhodium phosphate at a feed concentration of 0.3-3.3 wt. % in the presence of a gas stream comprising carbon monoxide and hydrogen under hydroformylation conditions sufficient to form a hydroformylation product stream comprising a butanediol intermediate, wherein the allyl alcohol stream comprises less than 98 wt. % allyl alcohol.

2. The process of claim 1, further comprising contacting the butanediol intermediate with a hydrogenation catalyst in the presence of hydrogen under hydrogenation conditions sufficient to form a hydrogenation product stream comprising 1,4-butanediol.

3. The process of claim 2, characterized by an allyl alcohol conversion of 80-100%.

4. The process of claim 2, characterized by a selectivity of 65-100%.

5. The process of claim 2, further comprising recovering 1,4-butanediol from the hydrogenation product stream.

6. The process of claim 1, wherein the allyl alcohol stream comprises one or more impurities selected from acetone, water, propionaldehyde, n-propanol, $C_{4+}$ hydrocarbons, $C_{1+}$ oxygenates and combinations thereof.

7. The process of claim 6, wherein the allyl alcohol stream comprises an acetone concentration in a range of 0 wt. % to 25 wt. % based on the total weight of the allyl alcohol stream, a water concentration in a range of 0 wt. % to 6 wt. % based on the total weight of the allyl alcohol stream, a propionaldehyde concentration in a range of 0 wt. % to 6 wt. % based on the total weight of the allyl alcohol stream, a n-propanol concentration in a range of 0 wt. % to 1 wt. % based on the total weight of the allyl alcohol stream, a $C_{4+}$ hydrocarbon concentration in a range of 0 wt. % to 5 wt. % based on the total weight of the allyl alcohol stream and $C_{1+}$ oxygenates concentration in a range of 0 wt. % to 11 wt. % based on the total weight of the allyl alcohol stream.

8. The process of claim 1, wherein the allyl alcohol stream comprises methanol in a methanol concentration of less than 100 ppm.

9. The process of claim 1, wherein the allyl alcohol stream comprises an acetone concentration of at least 0.25 wt. % based on the total weight of the allyl alcohol stream, a methanol concentration of less than 100 ppm based on the total weight of the allyl alcohol stream, a water concentration of at least 0.1 wt. % based on the total weight of the allyl alcohol stream, a propionaldehyde concentration of at least 0.25 wt. % based on the total weight of the allyl alcohol stream, or combinations thereof.

10. The process of claim 1, wherein the hydroformylation conditions comprise a hydroformylation temperature in a range of 20° C. to 100° C. and a hydroformylation pressure in a range of 20 psig (137,895 Pa) to 600 psig (4,136,854 Pa).

11. The process of claim 1, wherein the hydroformylation catalyst comprises a rhodium phosphate with a rhodium:phosphate molar ratio of 1:1-1.2:1.

* * * * *

UNITED STATES PATENT AND TRADEMARK OFFICE
CERTIFICATE OF CORRECTION

PATENT NO. : 9,809,518 B2
APPLICATION NO. : 15/352851
DATED : November 7, 2017
INVENTOR(S) : Daniel F. White et al.

It is certified that error appears in the above-identified patent and that said Letters Patent is hereby corrected as shown below:

In the Specification

Column 2    Line 19    Before "oxygenates", insert --$C_{1+}$--

Signed and Sealed this
Tenth Day of March, 2020

Andrei Iancu
*Director of the United States Patent and Trademark Office*